(12) United States Patent
Hennessy et al.

(10) Patent No.: US 12,233,234 B2
(45) Date of Patent: Feb. 25, 2025

(54) INFUSION LINE HARNESS

(71) Applicant: CareFusion 303, Inc., San Diego, CA (US)

(72) Inventors: Maurice James Hennessy, Limerick (IE); Ronald Hidalgo, Killaloe (IE); Andrei Reaboi, Limerick (IE); Warren Greer, Corbally (IE)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 17/709,286

(22) Filed: Mar. 30, 2022

(65) Prior Publication Data

US 2022/0323671 A1    Oct. 13, 2022

Related U.S. Application Data

(60) Provisional application No. 63/168,179, filed on Mar. 30, 2021.

(51) Int. Cl.
*A61M 5/14* (2006.01)
*F16L 3/10* (2006.01)
*F16L 3/26* (2006.01)

(52) U.S. Cl.
CPC ......... *A61M 5/1418* (2013.01); *F16L 3/1058* (2013.01); *F16L 3/26* (2013.01)

(58) Field of Classification Search
CPC .............. A61M 5/1418; A61M 5/1417; A61M 5/1415; A61M 5/1414; F16L 3/1058; F16L 3/26

(Continued)

(56) References Cited

U.S. PATENT DOCUMENTS 3,430,300 A * 3/1969 Mildred ................ A61M 25/02
                                                            24/304
4,795,429 A * 1/1989 Feldstein ............ A61M 5/1407
                                                            604/82

(Continued)

FOREIGN PATENT DOCUMENTS

CN       103845777 A      6/2014
CN       210844620 U      6/2020

OTHER PUBLICATIONS

Extended European Search Report for Application No. 22165521.0, dated Aug. 8, 2022, 24 pages.

*Primary Examiner* — Nkeisha Smith
(74) *Attorney, Agent, or Firm* — Morgan, Lewis & Bockius LLP

(57) ABSTRACT

An infusion line harness includes a rectangular material with first and second anchor tabs opposing ends of a first longitudinal edge of the rectangular material such as to extend the first longitudinal edge of the material to include a length of the first and second anchor tabs. The rectangular material includes one or more first fasteners positioned on the rectangular material along the first longitudinal edge and one or more complimentary fasteners positioned along the second longitudinal edge and which are configured to connect to the one or more first fasteners, the first fasteners and second fasteners being positioned such that when connected to each other the rectangular material forms a tubular structure. The first and second anchor tabs each are configured to wrap around a respective object and fasten to itself, or to a respective portion of the rectangular material, to anchor the harness to the respective object.

16 Claims, 6 Drawing Sheets

(58) Field of Classification Search
USPC .......................................................... 248/131
See application file for complete search history.

(56) References Cited

U.S. PATENT DOCUMENTS

| | | | | |
|---|---|---|---|---|
| 4,988,062 A * | 1/1991 | London | ................ | A61G 7/0503 604/80 |
| 5,224,932 A * | 7/1993 | Lappas | ................ | A61M 39/08 604/173 |
| 5,254,110 A * | 10/1993 | Marcus | ................ | A61G 7/0503 24/570 |
| 5,535,787 A * | 7/1996 | Howell | ................ | H02G 3/0487 248/205.2 |
| 5,709,665 A * | 1/1998 | Vergano | ................ | A61G 7/0503 604/179 |
| 5,836,453 A * | 11/1998 | Herrera | ................ | A61G 7/0503 5/503.1 |
| 5,964,252 A * | 10/1999 | Simmons | ................ | F16L 59/022 428/40.1 |
| 5,997,967 A * | 12/1999 | Hawkings | ................ | H02G 15/1813 428/36.9 |
| 6,026,811 A * | 2/2000 | Settle | ................ | A61M 16/0666 128/207.18 |
| 6,315,759 B1 * | 11/2001 | Peterson | ................ | A61M 5/14 428/36.5 |
| 6,419,660 B1 * | 7/2002 | Russo | ................ | A61M 25/02 128/DIG. 26 |
| 6,551,277 B1 * | 4/2003 | Ford | ................ | A61M 5/1456 604/152 |
| 7,632,249 B2 * | 12/2009 | Momeni | ................ | A61M 5/14232 604/154 |
| 8,034,424 B2 * | 10/2011 | Smith | ................ | B05B 13/0285 248/431 |
| 8,205,314 B1 * | 6/2012 | Dermody, IV | ................ | B21D 49/00 382/163 |
| 8,597,254 B1 * | 12/2013 | Mullet | ................ | A61M 5/1418 604/179 |
| 8,882,718 B2 * | 11/2014 | Mullet | ................ | A61M 25/02 604/164.08 |
| 9,052,042 B2 * | 6/2015 | May | ................ | F16L 57/06 |
| 9,248,225 B2 * | 2/2016 | Demers | ................ | G16H 20/40 |
| 9,386,824 B1 * | 7/2016 | Schultz | ................ | A44B 18/0084 |
| 9,675,843 B2 * | 6/2017 | Petty | ................ | A63B 29/02 |
| 10,092,689 B2 * | 10/2018 | McLeod | ................ | A61M 5/1413 |
| 10,105,482 B1 * | 10/2018 | Holland | ................ | A61M 39/08 |
| 10,232,107 B2 * | 3/2019 | Utz | ................ | F21V 33/0068 |
| 10,835,667 B1 * | 11/2020 | Rogers | ................ | A61M 5/1417 |
| 2012/0152998 A1 * | 6/2012 | Hyzdu | ................ | A45F 5/00 224/676 |
| 2013/0310771 A1 * | 11/2013 | Karlin | ................ | A61M 39/08 604/263 |
| 2014/0088511 A1 * | 3/2014 | Mullet | ................ | A61M 5/1626 604/164.08 |
| 2017/0023216 A1 * | 1/2017 | Utz | ................ | F21V 33/0068 |
| 2020/0023120 A1 | 1/2020 | Fischer | | |
| 2020/0276383 A1 | 9/2020 | Hartmann et al. | | |
| 2020/0338250 A1 | 10/2020 | Yuds et al. | | |

\* cited by examiner

INFUSION LINE HARNESS

CROSS-REFERENCE TO RELATED APPLICATION

This application claims the benefit of U.S. Provisional Application No. 63/168,179, filed on Mar. 30, 2021, the entirety of each of which is incorporated herein by reference for all purposes.

TECHNICAL FIELD

The present disclosure generally relates to systems and methods of organizing infusion lines.

BACKGROUND

Critical care patients often have numerous therapeutic connections (e.g. cords, cables, and tubes) at the bedside that can easily become disorganized and tangled, leading to contamination of the connections, nurse confusion, a physical hazard that increases the risk for falls for both nurses and patients, and the possibility of damage of medical devices.

SUMMARY

In order to improve the organization of infusion lines, and to prevent "infusion line spaghetti" an infusion line harness is disclosed. The disclosed infusion line harness includes a rectangular material with longitudinal edges of the material being longer than a width of the material. First and second anchor tabs are connected to the rectangular material at opposing ends of a first longitudinal edge of the rectangular material such as to extend the first longitudinal edge of the material to include a length of the first and second anchor tabs, the anchor tabs each being narrower than a width of the rectangular material such that a second longitudinal edge of the rectangular material is not extended by the first and second anchor tabs. The rectangular material may have one or more first fasteners positioned on the rectangular material along the first longitudinal edge and one or more complimentary fasteners positioned on the rectangular material along the second longitudinal edge and which are configured to connect to the one or more first fasteners, the first fasteners and second fasteners being positioned such that when connected to each other the rectangular material forms a tubular structure. When the first and second fasteners are connected to form the tubular structure from the rectangular material, the first and second anchor tabs may protrude from the tubular structure. The first and second anchor tabs may each be configured to wrap around a respective object and fasten to itself, or to a respective portion of the rectangular material, to anchor the rectangular material to the respective object.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE FIGURES

The accompanying drawings, which are included to provide further understanding and are incorporated in and constitute a part of this specification, illustrate disclosed embodiments and together with the description serve to explain the principles of the disclosed embodiments. In the drawings.

DESCRIPTION

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
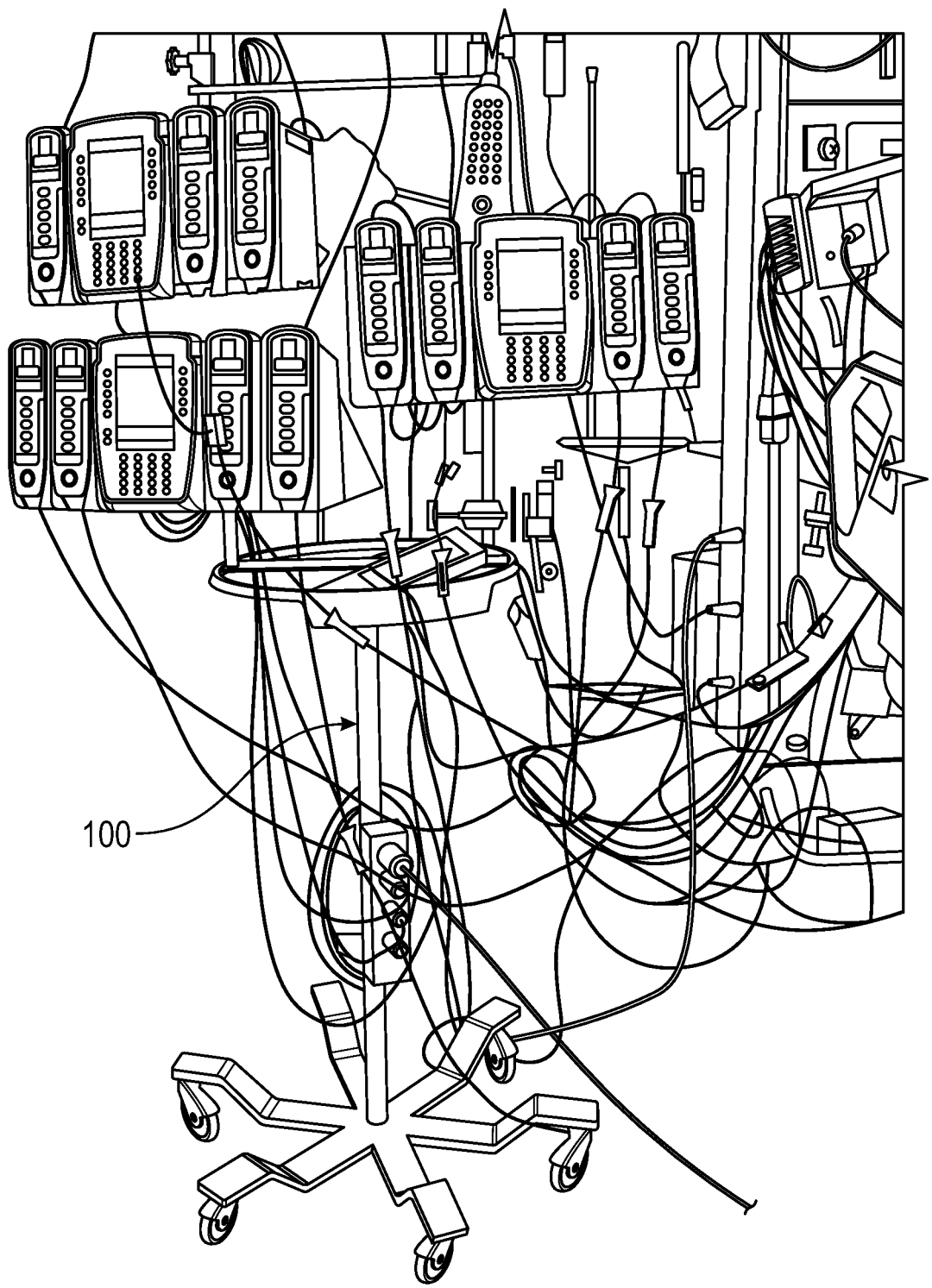
FIG. 1 depicts an intravenous (IV) pole with multiple infusion devices (including pumps) hanging therefrom.

FIG. 1 depicts an intravenous (IV) pole 100 with multiple infusion devices (including pumps) hanging therefrom. Each infusion device may include multiple pumps and thus multiple infusion lines. In an intensive care unit (ICU) or emergency room environment multiple infusion devices may be hung or attached to a single IV pole. When multiple infusion lines are connected to each infusion device (e.g. by way of multiple infusion modules) the infusion lines may become entangled with each other and it becomes more difficult to determine which line is connected to which device (or module). This scenario is commonly known as "infusion line spaghetti".

Individual clasp type organizers which may organize a limited amount of infusion lines (e.g. four) at a single point in the lines are difficult to implement in an emergency environment and do not prevent entanglement or twisting of the infusion lines between each organizer. Such organizers also do not bridge the cap between the IV pole and the patient bed, and thus do not address the "spaghetti" of lines from the IV pole to the patient.

The subject technology manages and organizes infusion lines and thereby reduces clutter and potential risks involved with identifying misplaced or defective infusion lines. The subject technology includes an infusion harness that continuously harnesses multiple infusion lines and anchors to an IV pole on one edge and the patient's bed on the other edge.

Figure 2A:
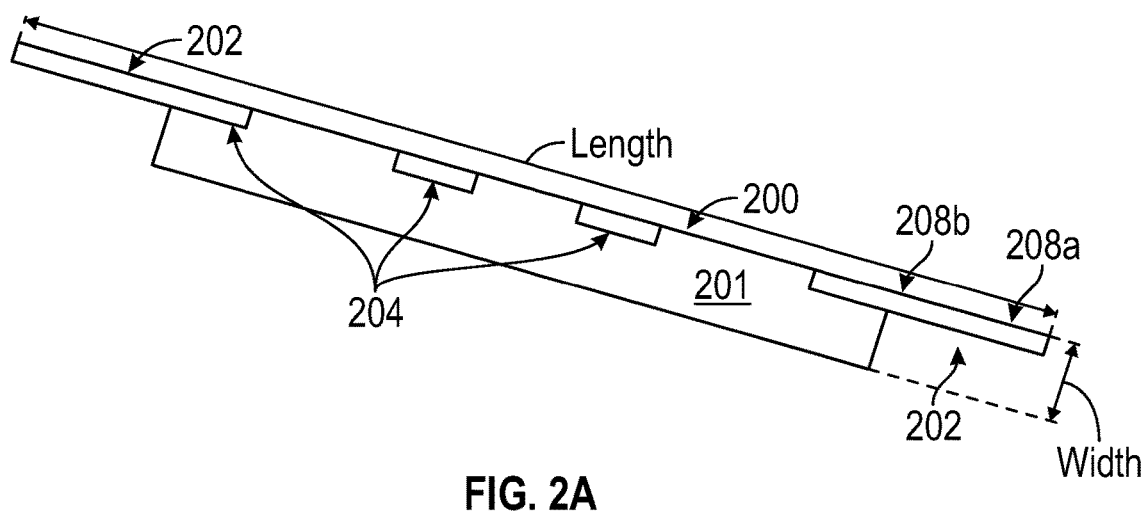
FIGS. 2A and 2B depict an example infusion line harness, according to various aspects of the subject technology.
Figure 2B:
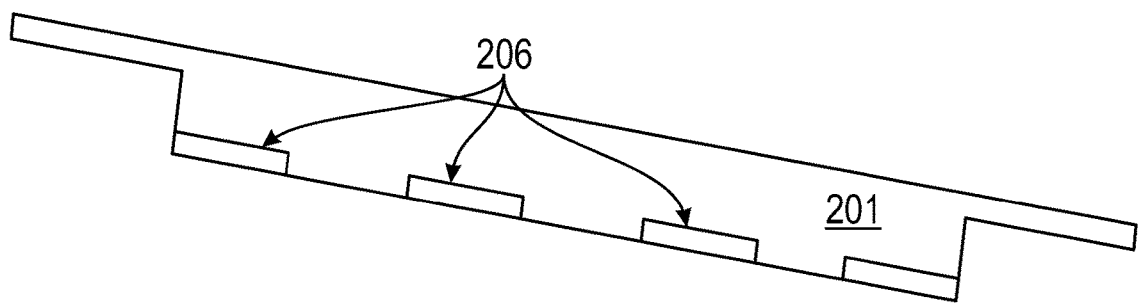

FIGS. 2A and 2B depict an example infusion line harness, according to various aspects of the subject technology. The disclosed harness 200 is constructed from a rectangular material with longitudinal edges of the material being longer than a width of the material. In this regard, harness 200 may include a rectangular portion 201 and anchor tabs 202. First and second anchor tabs 202 are connected to the rectangular portion at opposing ends of a first longitudinal edge of the rectangular material such as to extend the first longitudinal edge of the material to include a length of the first and second anchor tabs, the anchor tabs each being narrower than a width of the rectangular material such that a second longitudinal edge of the rectangular material is not extended by the first and second anchor tabs. In some implementations, anchor tabs 202 are connected to rectangular portion 201 by way of being a single continuous piece of material or stitched or connected together to be considered the equivalent of a single piece of material.

Figure 3A:
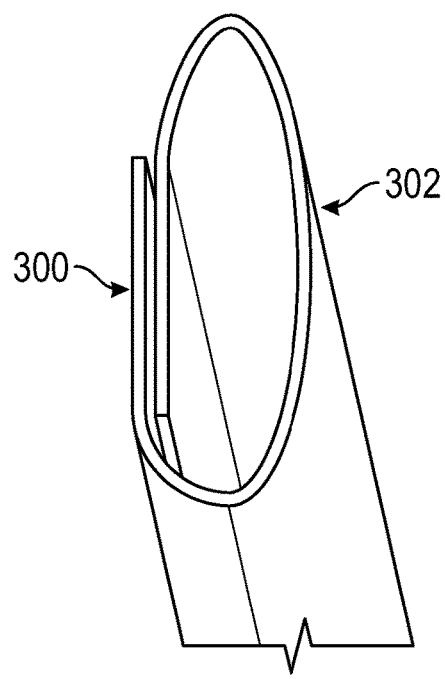
FIGS. 3A to 3C depict various features of the disclosed infusion line harness, according to various aspects of the subject technology.

According to various aspects, the rectangular material has one or more first fasteners 204 positioned on the rectangular material along the first longitudinal edge and one or more complimentary fasteners 206 positioned on the rectangular material along the second longitudinal edge and which are configured to connect to the one or more first fasteners 204. The first fasteners and second fasteners are positioned such that when connected to each other the rectangular material forms a tubular structure, as seen in FIG. 3A. For example, as depicted in FIGS. 2A and 2B, first fasteners 204 may be on a first surface of the material near the first longitudinal edge (or spine of the harness) and second fasteners 206 may be on the other surface, opposite the first surface, near the opposing second longitudinal edge. In this manner, the rectangular portion of the material may be folded over upon itself to form the tubular structure of FIG. 3A.

The material may be a washable cloth material such as a medical-grade polypropylene fabric or marine vinyl. In this regard, the harness may be washed and/or sterilized after use and reused again. The material may also be a clear flexible polymer or PVC based vinyl. According to various implementations, an opaque material may provide protection for light sensitive drugs.

In the depicted example, fasteners 204 and 206 are hook-and-pile or hook-and-loop fastener such as Velcro. However, fasteners 204 and 206 may also include a plurality of snap fasteners (e.g. snap buttons) or a plurality of opposite polarity magnets. A respective snap fastener (also called press stud, popper, snap or tich) may include pair of interlocking discs, made out of a metal or plastic, commonly used in place of traditional buttons to fasten clothing and for similar purposes.

In some implementations, fasteners 204 and/or 206 may a plurality of magnets or a magnetized material. For example, fasteners 204 (or 206) may include ferromagnetic material or vinyl magnetic sheet while fasteners 206 (or 204) including a magnetic attractive material or a like magnet having an opposite polarity. In some implementations, fasteners 204 and 206 may also include interlocking grooves and ridges that fasten or seal together such as in press and seal freezer storage bag.

With reference to FIG. 2A, each respective anchor tab 202 may include one or more fasteners 208. Each fastener 208 is configured so that a first end 208 *a* (e.g., beginning) of a respective anchor tab 202 may fold over and attach to a second end 208 *b* of the other respective anchor tab 202. As will be described further, this configuration allows each respective anchor tab 202 to be anchored to a respective object by wrapping around the object and fastening to itself. Fastener 208 may be a continuous fastener such as a hook-and-pile or hook-and-loop fastener, or may be two separate fasteners at each of the first end 208 *a* and the second end 208 *b*. Fasteners 208 may be implemented by any of foregoing the fastener configurations of 204.

Figure 3B:
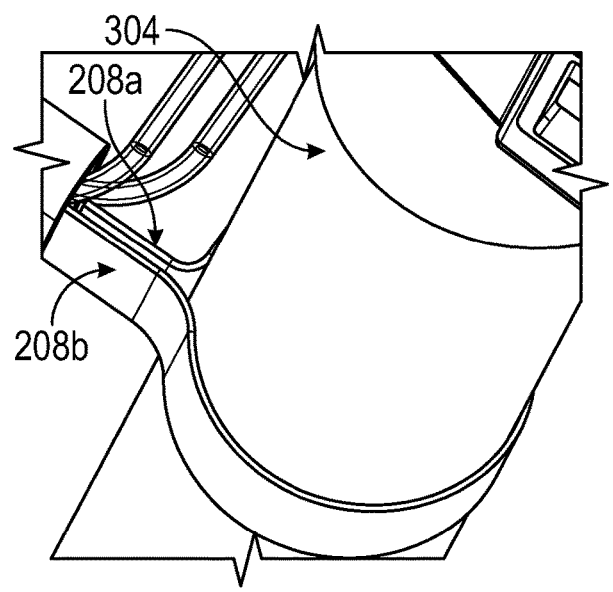
Figure 3C:
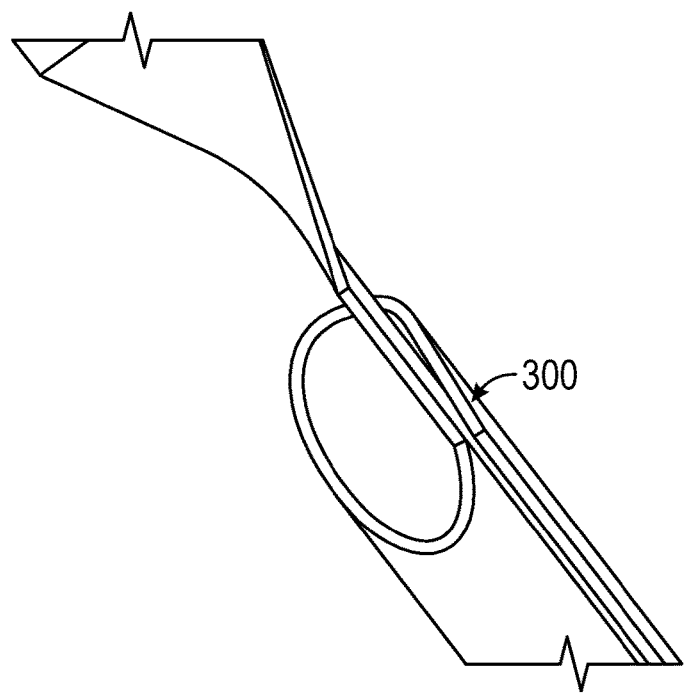

FIGS. 3A to 3C depict various features of the disclosed infusion line harness, according to various aspects of the subject technology. As disclosed above, first fasteners 204 and second fasteners 206 may be positioned on opposing sides at opposing edges so that the rectangular portion of the material may be folded over upon itself 300 to form a tubular structure 302. Having overlapping portions 300 retains the infusion lines securely within the harness and allows for opening of the harness for quick access to the lines, for example to add or remove lines therefrom. A clinician may open the harness sleeve and route IV lines therethrough.

When first fasteners 204 and second fasteners 206 are connected to form the tubular structure 302, the first and second respective anchor tabs 202 protrude from the tubular structure, as seen in FIGS. 3B and 3C. As depicted in FIG. 3B, the first and second anchor tabs are each configured to wrap around a respective object 304 and fasten to itself, or to a respective portion of the rectangular material, to anchor the rectangular material to object 304. According to various implementations, object 304 is 1-3 inches in diameter, and each anchor tab is 9-12 inches in length, leaving respective portions of anchor tab 202 at the first end 208 *a* and at the second end 208 *b* of anchor tab 202 for fasteners 208. The disclosed anchor fasteners 208 provide secure mounting to IV poles and to a patients bed, as will be described further with respect to FIGS. 4A to 4C.

Figure 4A:
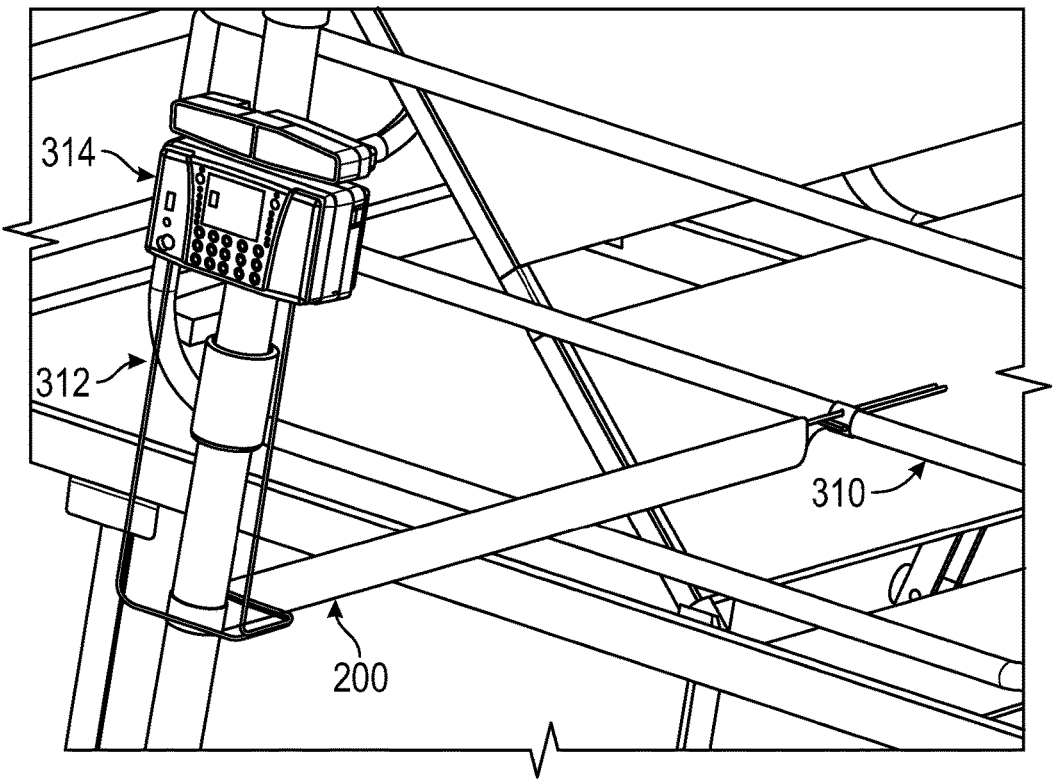
FIGS. 4A to 4C depict various connection features of the disclosed infusion line harness, according to various aspects of the subject technology.
Figures 4B, 4C:
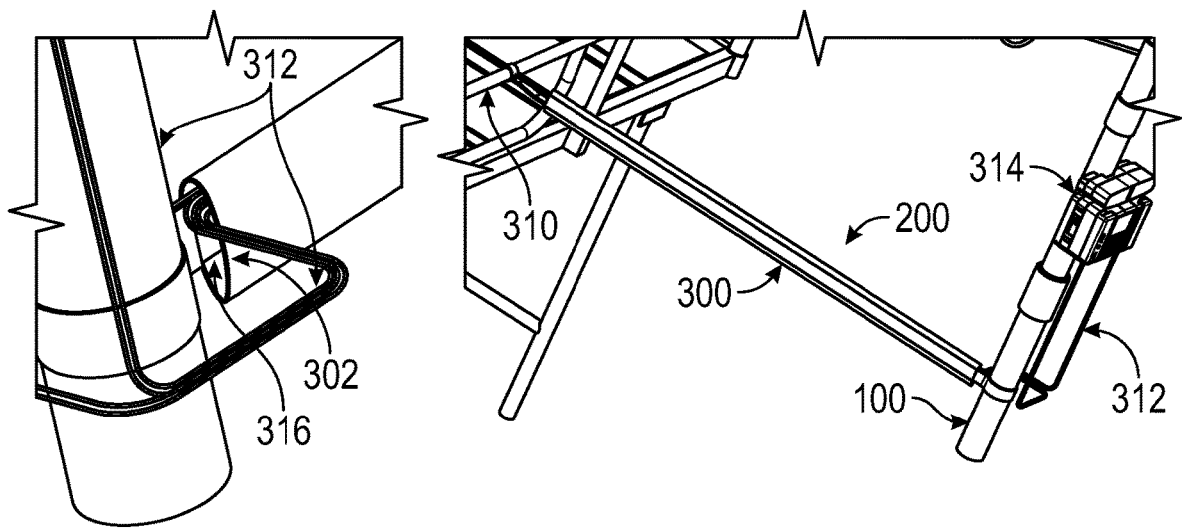

FIGS. 4A to 4C depict various connection features of the disclosed infusion line harness, according to various aspects of the subject technology. FIG. 4A depicts, from a front side of infusion harness 200, a first respective anchor tab 202 of infusion harness 200 being connected to an IV pole 100 and a second respective anchor tab 202 of infusion harness 200 being connected to a frame 310 of a patient bed. FIG. 4B depicts the same connection from a rear side of infusion harness 200. In the depicted example, infusion lines 312 exit an infusion device 314 and are routed through the hollow chamber 316 formed by tubular structure 302.

The example routing of infusion lines depicted by FIGS. 4A to 4C is useful to manage and organize infusion lines 312 in critical care situations. Additionally, anchoring harness 200 to IV pole 100 and bed frame 310 and placing the infusion lines therein minimizes the risk of tripping over a spaghetti of infusion lines, and minimizes the risk of infusion line "pulls". Furthermore, the rick of contamination of the lines and potential for infections is reduced because the lines are lifted off of the ground. Moreover, consolidation of multiple IV lines into one strand improves access to and room around the patient.

According to various implementations, harness 200 may, on the rectangular portion 201, include one or more unobstructed portions (not shown), and opaque portions. The unobstructed portions may, for example, be of include a window (in between or through the opaque portions) for viewing an interior of the tubular structure 300 and infusion lines 312 within the tubular structure, and the opaque portions facilitate placement of the infusion lines through the tubular structure. The unobstructed portions may be cutouts within the material, the remaining portion of the material making up the opaque portions.

In some implementations, harness 200 may further include a plurality of tabs (not shown), each tab being a different color. Each color may be representative of a medication or fluid type that is commonly used in infusions. For example, red may be representative of an opioid, yellow of an antibiotic, and green a saline solution. In this regard, only tabs having colors representative of the lines within the harness may be exposed to indicate to a clinician which infusion lines are being routed through the harness. The colored tabs may be accents on the material or built into the material. For example, the colored tabs may be appendages attached to rectangular portion 201 of harness 200. The tab appendages may be hidden within chamber 316 when not in use and selected tab appendages pulled out and exposed (to stick out) from overlap 300 to designate a type of infusion line within the harness.

In some implementations, the colored tabs may be fastened to fasteners 204. For example, in button implementations, each tab may have a cutout for a respective button so that the tab may be overlaid or clipped onto a button, with the button passing through the cutout. When corresponding buttons are snapped together the tab is fixed in place. In some implementations, the tabs may be clipped onto a portion of harness 200, or clipped onto a button designated for the tab (separate from fasteners 204, 206). In some implementations, the tabs may include a dual sided hook-and-pile or hook-and-loop fastener that may be placed in between like fasteners 204 and 206. The colored tabs may be made of a colored material such as the same material as harness 200, or a soft rubber.

In some implementations, harness 200 may include one or more transparent pockets (not shown) on an outer surface of the rectangular portion 201. In this regard, when the tubular structure is formed, the transparent pockets may be positioned on an external surface of the tubular structure. Each transparent pocket may be configured to hold a corresponding tab (e.g. described above) therein and to display each respective tab through the pocket. Thus, the pockets may be utilized for the same or similar purposes as the previously described colored tabs. Additionally, or in the alternative, the transparent pockets may be configured to hold a colored card, or a card that may be written on (e.g. by a sharpie) to designate the infusion lines held by harness 200.

Figures 5A, 5B:
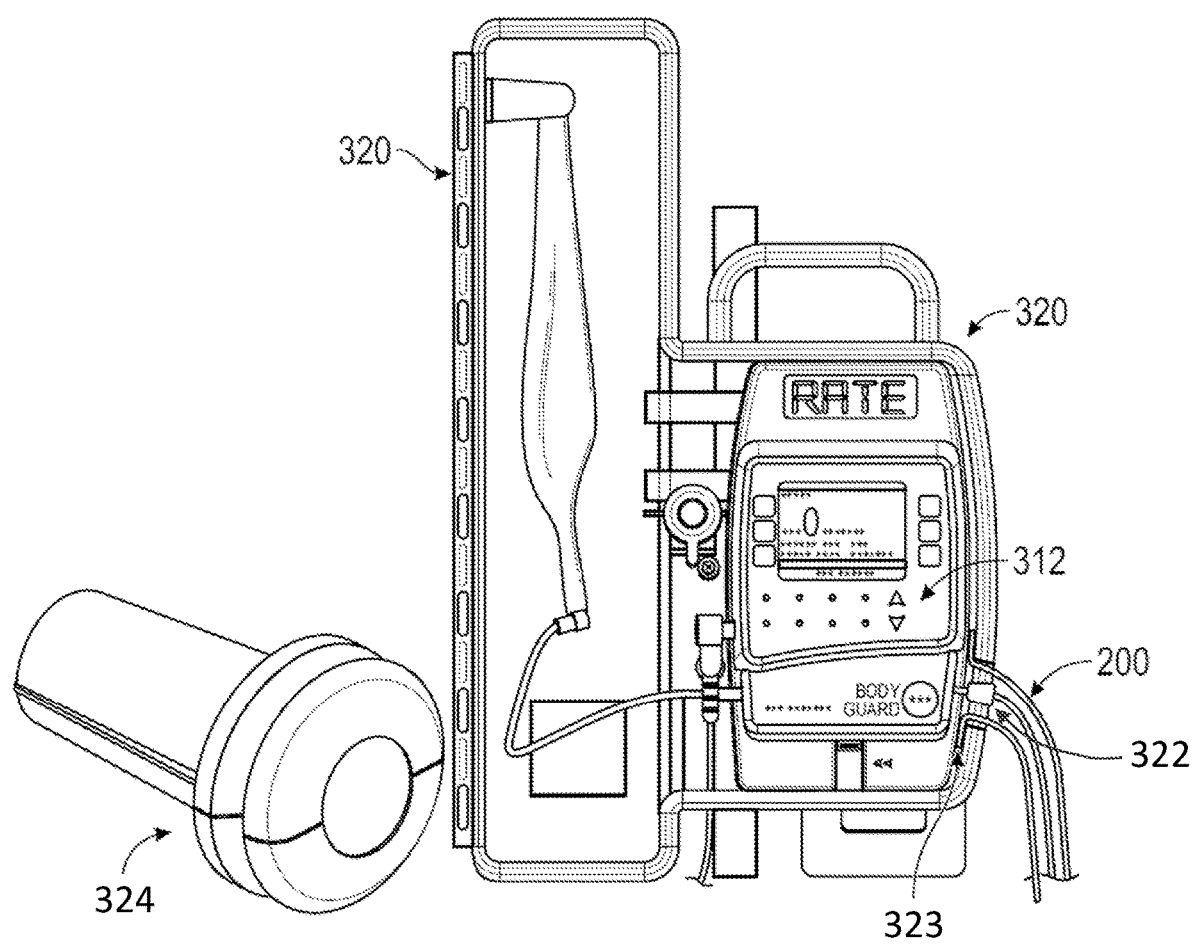
FIG. 5A depicts the disclosed harness connected to a infusion lock box, according to various aspects of the subject technology.
FIG. 5B depicts an example eyelet of the disclosed infusion lockbox.

FIG. 5 depicts the disclosed harness connected to an infusion lock box, according to various aspects of the subject technology. When controlled substances are involved, an IV bag 318 and a pump 312 may be installed into a medicine lock box 320 to prevent tampering with the pump settings or the substance, or to prevent diversion of the controlled substance. However, the IV line may not be shielded once it leaves pump 312.

According to some implementations, harness 200 may be connected through an eyelet 322 (FIG. 5B) of the lockbox 320 surrounding an infusion device and secured to an interior portion of the medicine lock box. In this regard, a respective anchor tab 202 may be internally secured and a portion of tubular section 302 passed through the eyelet 322. Harness 200 may be of a length long enough to traverse the infusion line from the pump to the patient bed. In this manner, the infusion line may be secured (at least partially) or hidden from sight from pump 312 to the patient bed. In some implementations, a grommet 324 may be installed into a side of the lockbox where the infusion line enters to further protect or seal harness 200.

According to some implementations, infusion pump 312 may include an anchor point on an external surface of the infusion pump (similar to a fastener 204, 206, or 208). In some implementations, the anchor point 323 may be on a portion of the pump 312 within or surrounded by lock box 320. The anchor point 323 may be disposed on the external surface to receive a first anchor tab of harness 200. Pump 312 may further include a fluid tubing pathway (e.g., an eyelet 322) directing a fluid tube received therein toward the harness 200. As described previously, lock box 320 may include eyelet 322. Eyelet 322 may be shaped to receive the first anchor tab and a portion of a tubular structure of the infusion harness 200. After receipt by eyelet 322, the first anchor tab and the portion of the tubular structure may be fully enclosed by lock box 320. In some implementations, the portion of the tubular structure and/or harness 200 may be anchored to the anchor point 323 (e.g. by a respective anchor tab 202) before the lock box is fully placed over pump 312 to enclose pump 312.

Figure 6:
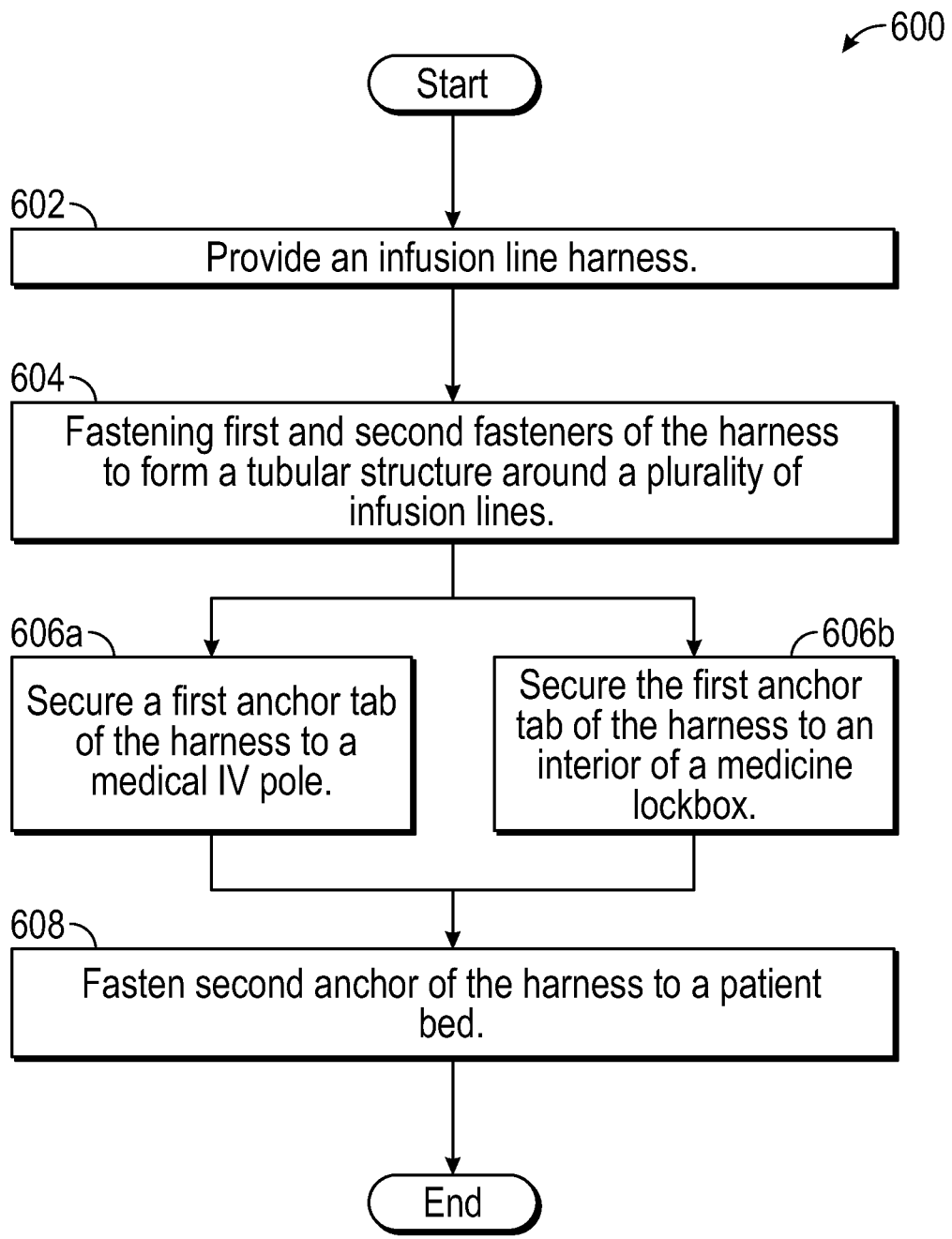
FIG. 6 depicts an example process for implementing the disclosed infusion harness, according to aspects of the subject technology.

FIG. 6 depicts an example process 600 for implementing the disclosed infusion harness 200, according to aspects of the subject technology. For explanatory purposes, the various blocks of example process 800 are described herein with reference to FIGS. 1 to 5, and the components and/or processes described herein. In some implementations, one or more of the blocks may be implemented apart from other blocks. Further for explanatory purposes, the blocks of example process 600 are described as occurring in serial, or linearly. However, multiple blocks of example process 600 may occur in parallel. In addition, the blocks of example process 600 need not be performed in the order shown and/or one or more of the blocks of example process 600 need not be performed.

In the depicted example, an infusion line harness 200 is provided (602). Infusion line harness 200 may include any of the foregoing features described with respect to FIGS. 1 through 5. Harness may include a rectangular material with longitudinal edges of the material being longer than a width of the material. First and second anchor tabs are connected to the rectangular material at opposing ends of a first longitudinal edge of the rectangular material such as to extend the first longitudinal edge of the material to include a length of the first and second anchor tabs, the anchor tabs each being narrower than a width of the rectangular material such that a second longitudinal edge of the rectangular material is not extended by the first and second anchor tabs. The rectangular material may have one or more first fasteners positioned on the rectangular material along the first longitudinal edge and one or more complimentary fasteners positioned on the rectangular material along the second longitudinal edge and which are configured to connect to the one or more first fasteners, the first fasteners and second fasteners being positioned such that when connected to each other the rectangular material forms a tubular structure. When the first and second fasteners are connected to form the tubular structure from the rectangular material, the first and second anchor tabs may protrude from the tubular structure. The first and second anchor tabs may each be configured to wrap around a respective object and fasten to itself, or to a respective portion of the rectangular material, to anchor the rectangular material to the respective object.

The first and second fasteners are fastened to form the tubular structure with the plurality of infusion lines passing therethrough (604). The first anchor tab is then secured, in the manner previously described, to a medical IV pole supporting a plurality of medical devices providing a fluid to the plurality of infusing lines (606a). Additionally or in the alternative, the first anchor tab and a portion of the tubular structure is passed through a eyelet of a medicine lock box surrounding an infusion device providing a fluid to at least one of the plurality of infusion lines and the first anchor tab is secured to an interior portion of a medicine lock box (606b). The second anchor tab is fastened to a portion of a patient bed (608) in the manner previously described.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An infusion line harness, comprising: a rectangular material with longitudinal edges of the material being longer than a width of the material; first and second anchor tabs connected to the rectangular material at opposing ends of a first longitudinal edge of the rectangular material such as to extend the first longitudinal edge of the material to include a length of the first and second anchor tabs, the anchor tabs each being narrower than a width of the rectangular material such that a second longitudinal edge of the rectangular material is not extended by the first and second anchor tabs; wherein the rectangular material has one or more first fasteners positioned on the rectangular material along the first longitudinal edge and one or more complimentary fasteners positioned on the rectangular material along the second longitudinal edge and which are configured to connect to the one or more first fasteners, the first fasteners and second fasteners being positioned such that when connected to each other the rectangular material forms a tubular structure; wherein, when the first and second fasteners are connected to form the tubular structure from the rectangular material, the first and second anchor tabs protrude from the tubular structure, and wherein the first and second anchor tabs are each configured to wrap around a respective object and fasten to itself, or to a respective portion of the rectangular material, to anchor the rectangular material to the respective object.

Clause 2. The infusion line harness of Clause 1, wherein the rectangular material comprises opaque portions and unobstructed portions, wherein the unobstructed portions provide a window for viewing an interior of the tubular structure and infusion lines within the tubular structure, and the opaque portions facilitate placement of the infusion lines through the tubular structure.

Clause 3. The infusion line harness of Clause 1 or Clause 2, further comprising: a plurality of tabs, each tab being a different color.

Clause 4. The infusion line harness of any one of Clauses 1 through 3, further comprising: one or more transparent pockets on a surface of the rectangular material, wherein, when the tubular structure is formed, the transparent pockets are positioned on an external surface of the tubular structure, and wherein each transparent pocket is configured to hold a corresponding tab and to display each respective tab through the pocket.

Clause 5. The infusion line harness of any one of Clauses 1 through 4, wherein the first and second fasteners collectively fasten or seal together with interlocking grooves and ridges.

Clause 6. The infusion line harness of any one of Clauses 1 through 4, wherein the first and second fasteners collectively comprise a plurality of snap fasteners.

Clause 7. The infusion line harness of any one of Clauses 1 through 4, wherein the first and second fasteners comprise one or more magnetic fasteners.

Clause 8. An infusion pump comprising: an anchor point on an external surface of the infusion pump, the anchor point disposed on the external surface to receive a first anchor tab of an infusion harness according to any one of Clauses 1 through 7; and a fluid tubing pathway directing a fluid tube received therein toward the infusion harness.

Clause 9. The infusion pump of Clause 8, further comprising a medicine lock box surrounding at least a portion of the infusion pump, the portion of the infusion pump including the anchor point.

Clause 10. The infusion pump of Clause 9, wherein the medicine lock box includes an eyelet shaped to receive the first anchor tab and a portion of a tubular structure of the infusion harness, wherein, after receipt by the eyelet, the first anchor tab and the portion of the tubular structure are enclosed by the medicine lock box.

Clause 11. A method comprising: wrapping a plurality of infusion lines with the rectangular material of the infusion line harness of Clause 1; fastening the first and second fasteners to form the tubular structure with the plurality of infusion lines passing therethrough; securing the first anchor tab to a medical intravenous pole supporting a plurality of medical devices providing a fluid to the plurality of infusing lines; and securing the second anchor tab to a portion of a patient bed.

Clause 12. A method comprising: wrapping a plurality of infusion lines with the rectangular material of the infusion line harness of Clause 1; fastening the first and second fasteners to form the tubular structure with the plurality of infusion lines passing therethrough; passing the first anchor tab and a portion of the tubular structure through a eyelet of a medicine lock box surrounding an infusion device providing a fluid to at least one of the plurality of infusion lines and securing the first anchor to an interior portion of the medicine lock box; and securing the second anchor tab to a portion of a patient bed.

Further Consideration

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by any claim. Furthermore, to the extent that the term "include," "have," or the like is used in the description, such term is intended to be inclusive in a manner similar to the term "comprise" as "comprise" is interpreted when employed as a transitional word.

What is claimed is:

1. An infusion system, comprising:
    an infusion line harness comprising a material forming a tubular structure and having at least one anchor tab connected to the material at an end of the tubular structure such as to extend a longitudinal edge of the material;
    an infusion pump comprising an anchor point on an external surface of the infusion pump, the anchor point disposed on the external surface and configured to fasten to the at least one anchor tab of an infusion line harness; and
    a medicine lock box securely enclosing at least a portion of the infusion pump that comprises the anchor point, the medicine lock box comprising a fluid tubing pathway in the form of an eyelet shaped to receive the at least one anchor tab and a portion of a tubular structure of the infusion line harness,
    wherein, the at least one anchor tab and the portion of the tubular structure are received by the eyelet such that the at least one anchor tab and the portion of the tubular structure are enclosed by the medicine lock box.

2. The infusion system of claim 1, wherein the infusion line harness comprises:
    a rectangular material with longitudinal edges of the material being longer than a width of the material;
    wherein the at least one anchor tab comprises first and second anchor tabs connected to the rectangular material at opposing ends of a first longitudinal edge of the rectangular material such as to extend the first longitudinal edge of the material to include a length of the first and second anchor tabs, the first and second anchor tabs each being narrower than a width of the rectangular material such that a second longitudinal edge of the rectangular material is not extended by the first and second anchor tabs;
    wherein the rectangular material has one or more first fasteners positioned on the rectangular material along the first longitudinal edge and one or more second fasteners positioned on the rectangular material along the second longitudinal edge and which are configured to connect to the one or more first fasteners, the first fasteners and second fasteners being positioned such that when connected to each other the rectangular material forms a tubular structure;
    wherein, when the first and second fasteners are connected to form the tubular structure from the rectangular material, the first and second anchor tabs protrude from the tubular structure, and
    wherein the first and second anchor tabs are each configured to wrap around a respective object and fasten to itself, or to a respective portion of the rectangular material, to anchor the rectangular material to the respective object.

3. The infusion system of claim 2, wherein the rectangular material comprises opaque portions and unobstructed portions, wherein the unobstructed portions provide a window for viewing an interior of the tubular structure and infusion lines within the tubular structure, and the opaque portions facilitate placement of the infusion lines through the tubular structure.

4. The infusion system of claim 2, wherein the infusion line harness comprises:
    a plurality of tabs, including the first and second anchor tabs, each tab being a different color.

5. The infusion system of claim 2, wherein the infusion line harness comprises:
    one or more transparent pockets on a surface of the rectangular material,
    wherein, when the tubular structure is formed, the transparent pockets are positioned on an external surface of the tubular structure, and
    wherein each transparent pocket is configured to hold a corresponding tab of a plurality of tabs and to display each corresponding tab through the transparent pocket.

6. The infusion system of claim 2, wherein the first and second fasteners collectively fasten or seal together with interlocking grooves and ridges.

7. The infusion system of claim 2, wherein the first and second fasteners collectively comprise a plurality of snap fasteners.

8. The infusion system of claim 2, wherein the first and second fasteners comprise one or more magnetic fasteners.

9. A method comprising:
    wrapping a plurality of infusion lines with an infusion line harness, the infusion line harness comprising a rectangular material having one or more first fasteners positioned along a first longitudinal edge of the rectangular material and one or more second fasteners positioned along a second longitudinal edge of the rectangular material, and first and second anchor tabs connected to the rectangular material at opposing ends of the first longitudinal edge such as to extend the first longitudinal edge of the rectangular material to include a length of the first and second anchor tabs;
    fastening the first and second fasteners to form a tubular structure with the plurality of infusion lines passing therethrough;
    passing the first anchor tab and a portion of the tubular structure through a eyelet of a medicine lock box surrounding an infusion device providing a fluid to at least one of the plurality of infusion lines and securing the first anchor tab to an interior portion of the medicine lock box; and
    securing the second anchor tab to a portion of a patient bed.

10. The method of claim 9, wherein the infusion line harness comprises:
    the rectangular material with longitudinal edges of the material being longer than a width of the material, the first and second anchor tabs each being narrower than a width of the rectangular material such that a second longitudinal edge of the rectangular material is not extended by the first and second anchor tabs;

wherein, when the first and second fasteners are connected to form the tubular structure from the rectangular material, the first and second anchor tabs protrude from the tubular structure, and wherein the first and second anchor tabs are each configured to wrap around a respective object and fasten to itself, or to a respective portion of the rectangular material, to anchor the rectangular material to the respective object.

11. The method of claim 9, wherein the rectangular material comprises opaque portions and unobstructed portions, wherein the unobstructed portions provide a window for viewing an interior of the tubular structure and infusion lines within the tubular structure, and the opaque portions facilitate placement of the infusion lines through the tubular structure.

12. The method of claim 9, wherein the infusion line harness comprises:

a plurality of tabs, including the first and second anchor tabs, each tab being a different color.

13. The method of claim 9, wherein the infusion line harness comprises:

one or more transparent pockets on a surface of the rectangular material, wherein, when the tubular structure is formed, the transparent pockets are positioned on an external surface of the tubular structure, and wherein each transparent pocket is configured to hold a corresponding tab of the-a plurality of tabs and to display each corresponding tab through the transparent pocket.

14. The method of claim 9, wherein the first and second fasteners collectively fasten or seal together with interlocking grooves and ridges.

15. The method of claim 9, wherein the first and second fasteners collectively comprise a plurality of snap fasteners.

16. The method of claim 9, wherein the first and second fasteners comprise one or more magnetic fasteners.

* * * * *